United States Patent
Carroll

(10) Patent No.: US 6,746,681 B1
(45) Date of Patent: Jun. 8, 2004

(54) PET TOOTH CARE PREPARATION

(75) Inventor: David T. Carroll, Schofield, WI (US)

(73) Assignee: Preventive Dental Specialties, Inc., Weston, WI (US)

( * ) Notice: Subject to any disclaimer, the term of this patent is extended or adjusted under 35 U.S.C. 154(b) by 0 days.

(21) Appl. No.: 10/327,315

(22) Filed: Dec. 20, 2002

(51) Int. Cl.$^7$ ................................. A61K 7/16
(52) U.S. Cl. .................. 424/401; 424/49; 424/717
(58) Field of Search .............. 424/49–88, 401, 424/717

(56) References Cited

U.S. PATENT DOCUMENTS

| | | | | |
|---|---|---|---|---|
| 2,463,738 A | * | 3/1949 | Bernhart | 167/81 |
| 2,798,023 A | * | 7/1957 | Berger | 167/81 |
| 2,980,588 A | * | 4/1961 | Larde | 167/81 |
| 3,087,857 A | | 4/1963 | Davis et al. | |
| 3,244,595 A | * | 4/1966 | Peigh | 167/81 |
| 3,929,987 A | * | 12/1975 | Cocopney et al. | 424/49 |
| 4,022,879 A | | 5/1977 | Dietrich | |
| 4,217,370 A | * | 8/1980 | Rawlings et al. | 426/98 |
| 4,537,765 A | | 8/1985 | Gaffar et al. | |
| 4,587,119 A | | 5/1986 | Bucke et al. | |
| 4,690,775 A | * | 9/1987 | Schott et al. | 252/312 |
| 4,714,612 A | | 12/1987 | Nakamura et al. | |
| 4,877,602 A | | 10/1989 | Uematsu et al. | |
| 4,943,429 A | * | 7/1990 | Winston et al. | 424/49 |
| 4,999,348 A | * | 3/1991 | Cioca et al. | 514/171 |
| 5,094,870 A | | 3/1992 | Scaglione et al. | |
| 5,126,137 A | | 6/1992 | Lambert | |
| 5,405,836 A | | 4/1995 | Richar et al. | |
| 5,552,176 A | * | 9/1996 | Marino | 426/641 |
| 5,714,161 A | * | 2/1998 | Crane | 424/439 |
| 5,965,153 A | * | 10/1998 | Allen | 424/442 |
| 5,904,928 A | | 5/1999 | Cyr et al. | |
| 6,506,366 B1 | * | 1/2003 | Leinen et al. | 424/49 |

* cited by examiner

Primary Examiner—Frederick F. Krass
(74) Attorney, Agent, or Firm—Stiennon & Stiennon

(57) ABSTRACT

A toothpaste preparation provides baking soda, Vitamins A, C, D, and E, Pyridoxine HCl, Thiamine HCl, within a gel base, and given a pet attractive odor by the addition of small quantities of liquid flavoring. The clear gel limits the unsightly appearance of the gel should it become adhered to the pet's fur.

9 Claims, No Drawings

PET TOOTH CARE PREPARATION

CROSS REFERENCES TO RELATED APPLICATIONS

Not applicable

STATEMENT AS TO RIGHTS TO INVENTIONS MADE UNDER FEDERALLY SPONSORED RESEARCH AND DEVELOPMENT

Not applicable

BACKGROUND OF THE INVENTION

The present invention relates to preparations for the treatment of animal teeth in general, and more particularly to such preparations which are applied through brushing.

The brushing of teeth on a regular basis can result in improved dental health. The motion of the bristles can dislodge decay-enhancing food particles, while at the same time massaging the gums to counteract gum disease. Humans, of course, have the manual dexterity and will to look after their teeth and gums by frequent brushing. Animals, on the other hand, do not have the foresight to care for their own dental health, nor do most animals have the physical ability to handle a toothbrush.

Yet, the owners of animals kept as pets develop a close attachment to their pets, and generally desire to see them live long and healthy lives. Although dogs and cats can never brush their own teeth, specialized toothbrushes which assist the pet owner in brushing a pet's teeth are available, such as the PET-A-DENT® toothbrush, available from Preventative Dental Specialities, Inc. of Weston, Wis., and disclosed in U.S. Pat. No. 5,511,273, the disclosure of which is incorporated by reference herein.

Although beneficial results may be obtained by brushing a pet's teeth with water alone or by dry brushing, an applied dog toothpaste or flavored liquid may be helpful in encouraging the pet to voluntarily participate in the brushing activity because of the attractive flavor of the material applied to the brush. These common pastes or liquids can sometimes be little more than dog treats, having little beneficial value in themselves. Moreover, opaque pastes can become adhered to the pet's fur, presenting an unsightly appearance.

What is needed is a preparation for use in the brushing of pet teeth which is conducive, to the pet's well-being, which promotes pet acceptance of the brushing activity, and which limits the unsightly aftermath of the brushing.

SUMMARY OF THE INVENTION

The pet toothpaste of this invention provides water-soluble vitamins within a transparent gel base and having an attractive odor for use in brushing a pet's teeth.

Is an object of the present invention to provide a pet toothpaste which is not harmful to the pet if swallowed in brushing quantities.

It is an additional object of the present invention to provide a pet toothpaste which has an attractive odor but minimal flavoring.

It is another object of the invention to provide a pet toothpaste which promotes the compliance of the pet in the brushing activity.

It is a further object of the present invention to provide a pet toothpaste which limits the unsightly appearance of stray paste which becomes adhered to the pet's fur.

Further objects, features and advantages of the invention will be apparent from the following detailed description when taken in conjunction with the accompanying drawings.

BRIEF DESCRIPTION OF THE DRAWINGS

Not applicable.

DESCRIPTION OF THE PREFERRED EMBODIMENTS

The pet toothpaste of this invention has a transparent gel base in which water soluble vitamins and scent producing compounds are included. The toothpaste is preferably packaged in a pump dispenser or tube, for ready dispensing onto a toothbrush for pet use, such as the PET-A-DENT pet toothbrush, available from Preventive Dental Specialties, Inc.

The transparent gel base is primarily propylene glycol, with a preservative, a gelling ingredient, and natural colors. The gel base may be of the type manufactured by Vets. Plus, Inc, of Knapp, Wis. and used in the preparation sold by Vets Plus, Inc. as Cal-C-Fresh. However, conventional transparent gel bases of various compositions from many manufacturers may be used.

The ranges of water soluble vitamins and other ingredients per one ounce (28.5 g) of toothpaste, are set out in Table I.

TABLE I

| Ingredient | Minimum | Maximum | Preferred | Purpose |
|---|---|---|---|---|
| Baking Soda | 2 g | 14.5 g | 7.12 g | control of odor causing bacteria |
| Vitamin A | 250 IU | 5000 IU | 1000 IU | Immune stimulant |
| Riboflavin | 0.1 mg | 10 mg | 0.5 mg | improve oral mucosal health |
| Pyridoxine HCI | 0.1 mg | 10 mg | 0.2 mg | improve oral mucosal health |
| Thiamine HCI | 0.1 mg | 10 mg | 0.2 mg | improve oral mucosal health |
| Vitamin C | 50 mg | 500 mg | 150 mg | Immune stimulant, helps maintain gum health |
| Vitamin D | 50 IU | 500 IU | 100 IU | Help absorb calcium |
| Vitamin E | 5 IU | 500 IU | 10 IU | Immune |

Other compositions combining water soluble vitamins and odor producing substances in a transparent gel base may be prepared according to this invention.

The base may be a glycerin or other viscous hume which holds the vitamins in suspension. The base gel is transparent or translucent, so that, if it does become adhered to the pet's fur, it will not present an unsightly appearance.

Baking soda may be added, and, if it is, in quantities of 2 percent to 20 percent by weight. In addition, linoleic acid, an essential fatty acid, may be added in quantities of from 10–50 milligrams per dose. A dose would be about 2–3 cc, corresponding to a single squirt or dollop out of a squeeze bottle dispenser. The toothpaste is dispensed, not as a liquid, not as a powder, but as a gel, of a consistency that, when squeezed onto the bristles of the brush, it adheres to the bristles, and does not run off. The consistency is thicker than mousse, similar to that of conventional human toothpaste. Very young pets, i.e., puppies and kittens, would be dispensed about half of a regular dose. The toothpaste can also be made age specific, giving different dosages for different pets at different stages of life, for example, by reducing the quantities of each ingredient, relative to the gel base, for a toothpaste which is going to be used in a targeted manner to for puppies and kittens. Alternatively, the young animal gel may be sold in a container which dispenses a smaller dollop or drop onto the toothbrush.

It should be noted that the selected levels of vitamins and other nutrients is a maintenance formula designed to supplement the nutritional needs of a dog or cat. The toothpaste does not need to be refrigerated. As a maintenance formula, the toothpaste does not give the pet all the daily allowance of the vitamins it requires, but supplements the pet's nutrition which is principally received through meals.

The toothpaste does, however, provide a healthful supplement to the pet, rather than being purely a dog or cat treat. The intent is, if a pet owner will go to the trouble to brush a pet's teeth using toothpaste, it is desirable to introduce to the pet a nutritional supplement that will do more than just assist in brushing the teeth.

The toothpaste is given an attractive odor, by the addition of conventional liquid flavorings, but in relatively small quantities, such that the animal will open its mouth and accept the introduction of the paste and the toothbrush, because of the appealing aroma, but that there is not so much taste that the pet will be aggressively chewing the brush in order to taste the paste.

The toothpaste may be supplied in an 8–10 oz tube. Some substances that may be used for scenting include peanut oil, for peanut butter smell, beef extract oil, chicken extract oil, or tuna oil. The quantity is around 50–100 milligrams of oils per tube, as a small quantity of scent can be effective throughout a large quantity of toothpaste.

For an average 30 pound dog, a single dose may provide the following approximate quantities of nutrients:

minerals: calcium 100 mg, phosphorus 70 mg, potassium 5 mg magnesium 5 mg, iron 2 mg, copper 100 micrograms, manganese 60 micrograms, zinc 1.5 milligrams, iodine 52 micrograms, cobolt 14 micrograms.

Vitamins: C 1000 IU (international units) water soluble and fat soluble A 1000 IU, D 100 IU, E 10 IU, K 10 IU.

Trace amounts of thiamnin 0.2 mg, riboflavin 0.5 mg, folic acid 40 micrograms, pantothenic acid 2 mg, niacin 2.3 mg, pyridoxine 0.2 mg, vitamin B12 5 micrograms, choline 50 milligrams.

It is understood that the invention is not limited to the particular construction and arrangement of parts herein illustrated and described, but embraces all such modified forms thereof as come within the scope of the following claims.

I claim:

1. A pet dentifrice, comprising:
   gel base animal attracting odor-causing substance, and combined within each total quantity of dentifrice of 28.5 g, the following additives:
      2 g to 14.5 g baking soda;
      250 IU to 5000 IU Vitamin A;
      0.1 mg to 10 mg Riboflavin;
      0.1 mg to 10 mg Pyridoxine HCl;
      0.1 mg to 10 mg Thiamine HCl;
      50 mg to 500 mg Vitamin C;
      50 mg to 500 mg Vitamin D; and
      5 IU to 500 IU Vitamin E.

2. A method for caring for the teeth of a pet animal, comprising the step of:
   applying to a toothbrush a dose of dentifrice comprised of a base, having therein baking soda, and an animal attracting odor-causing substance, and at least part of a daily allowance of vitamins for the pet animal; and
   brushing the teeth of the pet animal with the applied dentifrice on the toothbrush; and
   supplementing the nutrition of the pet animal with said dose of dentifrice.

3. The method of claim 2 wherein the dose of dentifrice is about 2–3 cc and wherein said at least part of a daily allowance of vitamins for the pet animal, comprises:
   250 IU to 5000 IU Vitamin A;
   0.1 mg to 10 mg Riboflavin;
   0.1 mg to 10 mg Pyridoxine HCl;
   0.1 mg to 10 mg Thiamine HCl;
   50 mg to 500 mg Vitamin C;
   50 mg to 500 mg Vitamin D; and
   5 IU to 500 IU Vitamin E
added to each 28.5 g of the dose of dentifrice.

4. The method of claim 2 wherein the amount of baking soda within each 28.5 g dose of dentifrice is 2 g to 14.5 g.

5. The method of claim 2 wherein said animal attracting odor-causing substance comprises 5 to 25 mg of an odor causing substance which has minimal flavor attractive to the pet animal.

6. The method of claim 2 wherein said animal attracting odor-causing substance comprises 5 to 25 mg of an odor causing substance selected from the group consisting of: peanut oil, beef extract oil, chicken extract oil, and tuna oil;
   added to each 28.5 g of the dose of dentifrice.

7. The method of claim 2 wherein said gel base is primarily propylene glycol combined with a preservative and a gelling agent.

8. The pet dentifrice of claim 1 further 5 to 25 mg of an odor causing substance melted from the group consisting of: peanut oil, beef extract oil, chicken extract oil, and tuna oil.

9. The pet dentifrice of claim 1 wherein the gel base is primarily propylene glycol combined with a preservative and a gelling agent.

* * * * *

UNITED STATES PATENT AND TRADEMARK OFFICE
CERTIFICATE OF CORRECTION

PATENT NO.    : 6,746,681 B1
DATED         : June 8, 2004
INVENTOR(S)   : David T. Carroll It is certified that error appears in the above-identified patent and that said Letters Patent is hereby corrected as shown below:

<u>Column 3,</u>
Line 52, "gel base" should be -- a gel base, --
Line 52, "animal" should be -- an animal --

<u>Column 4,</u>
Line 9, "animal," should be -- animal; --
Line 12, "a base," should be -- a gel base, --

Signed and Sealed this

Twenty-fourth Day of May, 2005

JON W. DUDAS
*Director of the United States Patent and Trademark Office*